United States Patent
Nagel et al.

(10) Patent No.: US 9,463,281 B2
(45) Date of Patent: Oct. 11, 2016

(54) MEDICAMENT CONTAINER

(75) Inventors: Thomas Nagel, Tharandt (DE); Rene Richter, Tharandt (DE); Robert Witt, Dresden (DE)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 1121 days.

(21) Appl. No.: 13/389,456

(22) PCT Filed: Aug. 20, 2010

(86) PCT No.: PCT/EP2010/062154
§ 371 (c)(1),
(2), (4) Date: Jun. 27, 2012

(87) PCT Pub. No.: WO2011/023632
PCT Pub. Date: Mar. 3, 2011

(65) Prior Publication Data
US 2012/0266875 A1    Oct. 25, 2012

(30) Foreign Application Priority Data

Aug. 27, 2009    (EP) .................................... 09010973

(51) Int. Cl.
| | |
|---|---|
| A61M 11/00 | (2006.01) |
| A61M 5/315 | (2006.01) |
| A61M 5/28 | (2006.01) |
| A61M 15/00 | (2006.01) |

(52) U.S. Cl.
CPC .......... A61M 5/31511 (2013.01); A61M 5/282 (2013.01); *A61M 15/0028* (2013.01)

(58) Field of Classification Search
CPC ........ A61J 1/10; A61J 1/1475; A61J 1/1406; A61J 2001/2055; A61M 5/31511; A61M 5/282; A61M 15/0028
USPC ........... 128/200.14, 200.23, 200.24, 203.12; 604/408, 212, 207, 500; 220/62.22, 220/62.21, 62.29, 62.11, 9.1, 9.2; 206/521; 141/114
See application file for complete search history.

(56) References Cited

U.S. PATENT DOCUMENTS

| | | | | |
|---|---|---|---|---|
| 3,078,755 | A | * | 2/1963 | Chace, Jr. ............................ 87/9 |
| 3,981,415 | A | * | 9/1976 | Fowler et al. ................... 222/95 |
| 4,055,201 | A | * | 10/1977 | Fowler et al. ................ 139/421 |
| 4,088,166 | A | * | 5/1978 | Miller ............................ 604/408 |
| 4,248,366 | A | * | 2/1981 | Christiansen ............... 224/148.6 |
| 4,597,425 | A | * | 7/1986 | Tally ............................. 222/107 |
| 4,854,481 | A | * | 8/1989 | Bohl et al. ....................... 222/94 |
| 5,366,125 | A | * | 11/1994 | Procido ......................... 224/622 |
| 5,474,527 | A | | 12/1995 | Bettinger |
| 5,787,542 | A | * | 8/1998 | Chien .......................... 15/244.3 |

(Continued)

FOREIGN PATENT DOCUMENTS

WO    2009069518 A1    6/2009

OTHER PUBLICATIONS

Form PCT/IB/326, Notification Concerning Transmittal of International Preliminary Report on Patentability.

*Primary Examiner* — Steven Douglas
(74) *Attorney, Agent, or Firm* — McDonnell Boehnen Hulbert & Berghoff LLP

(57) ABSTRACT

A medicament container for a liquid medicament is disclosed, the medicament container includes a flexible bag with an outlet, the bag surrounded by a braid, arranged for lengthening and narrowing when being pulled in longitudinal direction (L).

7 Claims, 1 Drawing Sheet

(56) References Cited

U.S. PATENT DOCUMENTS

| | | | |
|---|---|---|---|
| 5,845,994 A * | 12/1998 | Rice | 383/76 |
| 6,251,098 B1 * | 6/2001 | Rake et al. | 604/408 |
| 6,569,142 B1 * | 5/2003 | Yoon | 604/408 |
| 7,914,487 B2 * | 3/2011 | Davies et al. | 604/103 |
| 8,403,178 B2 * | 3/2013 | May et al. | 222/129 |
| 8,602,250 B2 * | 12/2013 | Berger et al. | 220/586 |
| 2002/0107472 A1 | 8/2002 | Thompson et al. | |
| 2008/0097152 A1 * | 4/2008 | Stefanchik et al. | 600/114 |

* cited by examiner

MEDICAMENT CONTAINER

CROSS REFERENCE TO RELATED APPLICATIONS

The present application is a 35 U.S.C. 371 National Application of PCT/EP2010/062154 filed Aug. 20, 2010, which claims priority to European Patent Application No. 09010973.7, filed Aug. 27, 2009, the entire contents of which are incorporated entirely herein by reference.

TECHNICAL FIELD

The invention relates to a medicament container for a liquid medicament, the medicament comprising a bag with an outlet.

BACKGROUND OF THE INVENTION

Many medicaments have to be injected into the body. This applies in particular to medicaments, which are deactivated or have their efficiency remarkably decreased by oral administration, e.g. proteines (such as insulin, growth hormones, interferons), carbohydrates (e.g. heparin), antibodies and the majority of vaccines. Such medicaments are predominantly injected by means of syringes, medicament pens or medicament pumps.

Some medicaments have to be administered by inhaling them from so called inhalers.

WO 2009/069518 A1 discloses an inhaler, wherein the medicament to be inhaled is stored in a bag shaped medicament container.

SUMMARY OF THE INVENTION

It is an object of the present invention to provide an improved medicament container.

The object is achieved by a medicament container according to claim 1.

Preferred embodiments of the invention are given in the dependent claims.

A medicament container for a liquid medicament according to the invention comprises a flexible bag with an outlet. The bag is surrounded by a braid, arranged for lengthening and narrowing when being pulled in longitudinal direction. Similar cylindrical braids are known as so called Chinese finger traps or extension sleeves consisting of meshwork, which are used for fixing fingers or toes when repositioning juxtaarticular radius fractures or when preparing an arthroscopy of the wrist joint. Such braids may consist of interwoven wire, fibre or even bamboo strips. By narrowing the cylindrical braid the bag is compressed and the liquid medicament stored inside is displaced and thereby delivered through the outlet. The inventive design allows for setting aside displacing mechanisms like piston rods thus avoiding friction. Due to the small part count the medicament container may be easily produced. The inventive medicament container is a lightweight design compared to an ampoule. The cylindrical braid exerts a uniform compression onto the whole bag surface. Since the outlet usually exhibits some kind of bottleneck, in particular when equipped with valves and/or injection needles, compression of the bag results in an internal pressure inside the bag. Since all parts of the bag are supported by the narrowed cylindrical braid the bag is kept from locally bloating due to internal pressure so delayed dripping due to relaxation of the bloated part is avoided after stopping to pull the braid. Furthermore, without the local bloating dosing may be performed with an improved precision. A dosage of the medicament is thereby determined by a travel of the end of the braid being pulled. The cylindrical braid serving as an actor does not get in contact with the liquid medicament or active ingredient as opposed to a stopper in a conventional syringe. The inventive design is less error-prone due to its uncomplex arrangement.

Since the narrowing of the cylindrical braid is limited there may remain a dead volume in the bag after fully extending the braid. In order to avoid the dead volume the bag may have a rigid core arranged inside, e.g. arranged in a longitudinal direction of the bag. Preferably, an external diameter of the rigid core essentially equals a minimum internal diameter of the cylindrical braid when it is extended to a maximum. This allows for emptying the bag with virtually no residual volume of medicament left inside which is particularly important with expensive medicaments.

The bag may either be positioned in the cylindrical braid or the cylindrical braid may be embedded in the bag during production.

The outlet may comprise an interface for receiving a hollow injection needle or an array of needles. Alternatively the needle may be integrated with the medicament container.

One end of the cylindrical braid opposite the end where the braid is pulled may be attached to one of the outlet, the injection needle and a housing in order to have a support for a counteractive force acting against the pull movement.

The medicament container may be part of an injection arrangement or an inhaler arrangement for delivering a liquid medicament to a human or an animal.

The injection arrangement may comprise a valve and a hollow needle for piercing a patient's skin, the valve and needle being arranged at the outlet of the medicament container. In case of a jet injector, instead of the needle, a jet nozzle may be arranged.

The medicament container may preferably be used for delivering one of an analgetic, an anticoagulant, insulin, an insulin derivate, heparin, Lovenox, a vaccine, a growth hormone, a peptide hormone, a proteine, antibodies and complex carbohydrates.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limitive of the present invention, and wherein.

DETAILED DESCRIPTION OF PREFERRED EMBODIMENTS

Figure 1:
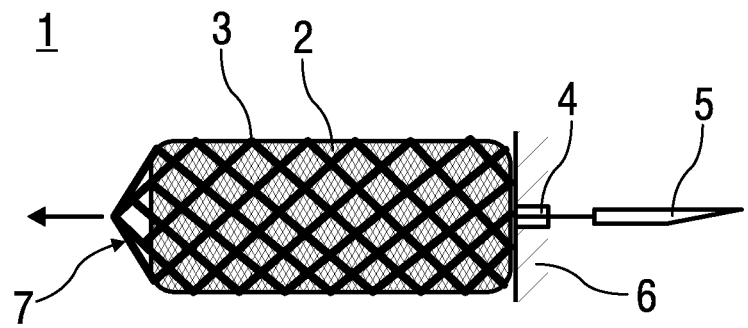
FIG. 1 is a medicament container with a flexible bag surrounded by a braid, the bag having an outlet connected to a hollow injection needle.

FIG. 1 shows a medicament container 1 with a flexible bag 2 surrounded by a braid 3. The bag 2 has an outlet 4 at a front end with a hollow injection needle 5 attached. The front end is supported by a housing 6 of the medicament container 1 or of an injection device which the medicament container 1 may be part of.

Figure 2:
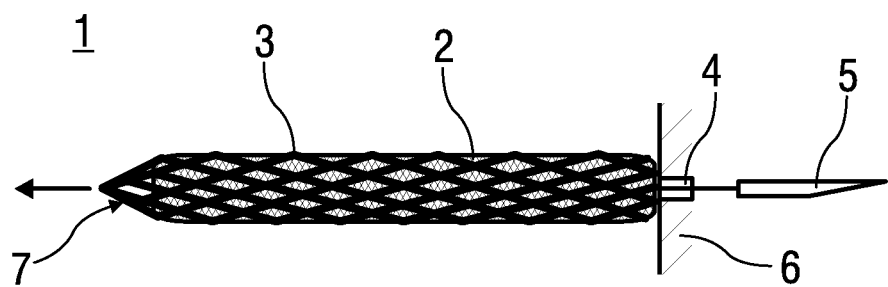
FIG. 2 is the medicament container of FIG. 1, the bag compressed by pulling and thus lengthening and narrowing the braid.

The braid 3 is arranged for lengthening and narrowing when being pulled in longitudinal direction L. A back end 7 of the braid 3 opposite the front end may be connected to a pull mechanism, e.g. by means of a hook. By narrowing the cylindrical braid 3 the bag 2 is compressed and the liquid medicament stored inside is displaced and thereby delivered through the outlet 4. This situation is shown in FIG. 2.

The bag 2 may have a rigid core inside (not shown), e.g. arranged in the longitudinal direction L of the bag 2. Preferably, an external diameter of the rigid core essentially equals a minimum internal diameter of the cylindrical braid 3 when the braid 3 is extended to a maximum.

The bag 2 may either be positioned in the cylindrical braid 3 after production of the bag 2 or the cylindrical braid 3 may be embedded in the bag 2 during production.

The outlet 4 may comprise an interface for receiving the hollow injection needle 5 or an array of needles. Alternatively the needle 5 may be integrated with the medicament container 1.

The front end of the cylindrical braid 3 opposite the back end 7 may be attached to one of the outlet 4, the injection needle 5 and the housing 6.

The medicament container 1 may be part of an injection arrangement or an inhaler arrangement for delivering a liquid medicament to a human or an animal.

The injection arrangement may comprise a valve and the hollow needle 5 for piercing a patient's skin, the valve and needle 5 being arranged at the outlet 4 of the medicament container 1. In case of a jet injector, instead of the needle 5, a jet nozzle may be arranged.

The medicament container 1 may preferably be used for delivering one of an analgetic, an anticoagulant, insulin, an insulin derivate, heparin, Lovenox, a vaccine, a growth hormone, a peptide hormone, a proteine, antibodies and complex carbohydrates.

The term "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, a antibody, an enzyme, an antibody, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exedin-3 or exedin-4 or an analogue or derivative of exedin-3 or exedin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-Y-glutamyl)-des(B30) human insulin; B29-N-(N-litho-cholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H His-Gly-Glu-Gly-Thr-Phe-Thr-Ser-Asp-Leu-Ser-Lys-Gln-Met-Glu-glu-Glu-Ala-Val-Arg-Leu-Phe-Ile-Glu-Trp-Leu-Lys-Asn-Gly-Gly-Pro-Ser-Ser-Gly-Ala-Pro-Pro-Pr-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;
or an Exendin-4 derivative of the sequence
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4 (1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2, H-Asn-(Glu)5-des Pro36, Pro37, Pro38 [Asp28] Exendin-4 (1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4 (1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2)25, Asp28] Exendin-4(1-39)-(Lys)6-NH2;
or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1 C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

LIST OF REFERENCES 1 medicament container
2 flexible bag
3 braid
4 outlet
5 hollow injection needle
6 housing
7 back end
L longitudinal direction

The invention claimed is:

1. Medicament container for a liquid medicament, the medicament container comprising a flexible bag with an outlet, the flexible bag surrounded by a braid, arranged for lengthening and narrowing when being pulled in a longitudinal direction, wherein one end of the braid is attached to one of the outlet and a housing, wherein the outlet comprises an interface for receiving a hollow injection needle.

2. Medicament container according to claim 1, characterized in that a rigid core is arranged in the flexible bag.

3. Medicament container according to claim 2, characterized in that the rigid core is arranged in a longitudinal direction with respect to the flexible bag.

4. Medicament container according to claim 3, characterized in that an external diameter of the rigid core essentially equals a minimum internal diameter of the braid when it is extended to a maximum extent.

5. Medicament container according to claim 1, characterized in that the braid is embedded in the flexible bag.

6. Injection arrangement for delivering a liquid medicament comprising the medicament container according to claim 1.

7. A method of using a medicament container according to claim 1 for delivering one of an analgetic, an anticoagulant, insulin, an insulin derivate, heparin, Lovenox, a vaccine, a growth hormone, a peptide hormone, a proteine, antibodies and complex carbohydrates comprising a step of providing the medicament container according to claim 1.

* * * * *